United States Patent
Goix et al.

(10) Patent No.: US 7,972,559 B2
(45) Date of Patent: Jul. 5, 2011

(54) PARTICLE OR CELL ANALYZER AND METHOD

(75) Inventors: Philippe J. Goix, Oakland, CA (US); Paul J. Lingane, Redwood City, CA (US); Janette T. Phi-Wilson, Los Altos Hills, CA (US); Kenneth F. Uffenheimer, Los Gatos, CA (US)

(73) Assignee: Millipore Corporation, Billerica, MA (US)

( * ) Notice: Subject to any disclaimer, the term of this patent is extended or adjusted under 35 U.S.C. 154(b) by 283 days.

(21) Appl. No.: 12/183,301

(22) Filed: Jul. 31, 2008

(65) Prior Publication Data

US 2008/0283773 A1 Nov. 20, 2008

Related U.S. Application Data

(60) Continuation of application No. 10/410,230, filed on Apr. 8, 2003, now Pat. No. 7,410,809, which is a division of application No. 09/844,080, filed on Apr. 26, 2001, now abandoned.

(60) Provisional application No. 60/230,380, filed on Sep. 6, 2000.

(51) Int. Cl.
*G01N 33/00* (2006.01)
(52) U.S. Cl. .............. 422/73; 422/68.1; 422/63; 422/50
(58) Field of Classification Search ................ 422/50, 422/63, 68.1, 73; 436/807, 809
See application file for complete search history.

(56) References Cited

U.S. PATENT DOCUMENTS

| | | |
|---|---|---|
| 3,192,969 A | 7/1965 | Baruch et al. |
| 3,827,304 A | 8/1974 | D'Autry |
| 4,318,884 A | 3/1982 | Suzuki |
| 4,448,752 A | 5/1984 | Banno et al. |
| 4,837,446 A | 6/1989 | Renard et al. |
| 5,132,088 A | 7/1992 | Wakatake |
| 5,135,302 A | 8/1992 | Hirako |
| 5,147,607 A | 9/1992 | Mochida |
| 5,178,750 A | 1/1993 | Mead |
| 5,424,037 A | 6/1995 | Zimmermann et al. |
| 5,495,105 A | 2/1996 | Nishimura et al. |
| 5,547,849 A | 8/1996 | Baer et al. |
| 5,548,395 A | 8/1996 | Kosaka |
| 5,656,499 A | 8/1997 | Chupp et al. |
| 5,814,277 A | 9/1998 | Bell et al. |
| 6,074,880 A | 6/2000 | Sutton et al. |

(Continued)

FOREIGN PATENT DOCUMENTS

JP 61-093932 5/1986

(Continued)

OTHER PUBLICATIONS

Derwent, D'Autry, "Analytical liquid sampling method-minimizing inter sample contamination and dead space," Derwent-ACC-No. 1973-26106U, Derwent-Week 197319; 2004 Derwent Information Ltd., 2004, File No. DWPI.

*Primary Examiner* — Melanie J Yu
(74) *Attorney, Agent, or Firm* — Houst Consulting (57) ABSTRACT

A particle analyzer in which tagged particles to be analyzed are drawn through a suspended capillary tube where a predetermined volume in the capillary tube is illuminated. The illumination scattered by said particles is detected by a detector to count all particles. The fluorescent illumination emitted by tagged particles is detected and the output signals from the fluorescent detectors and scatter detector are processed to provide an analysis of the particles.

7 Claims, 10 Drawing Sheets

U.S. PATENT DOCUMENTS

| | | | |
|---|---|---|---|
| 6,077,713 | A | 6/2000 | Dunfee et al. |
| 6,641,993 | B1 | 11/2003 | Jacobs et al. |
| 6,833,062 | B2 | 12/2004 | Kennedy et al. |
| 2003/0205472 | A1 | 11/2003 | Takahashi et al. |

FOREIGN PATENT DOCUMENTS

| | | |
|---|---|---|
| JP | 62-156856 | 10/1987 |
| JP | 63-135152 | 9/1988 |
| JP | 63-225143 | 9/1988 |
| JP | 01-240839 | 9/1989 |
| JP | 2-52237 | 2/1990 |
| JP | 3-185335 | 8/1991 |
| JP | 5-79970 | 3/1993 |
| JP | 5-232011 | 9/1993 |
| JP | 05-296914 | 11/1993 |
| JP | 5-312811 | 11/1993 |
| JP | 06-194299 A | 7/1994 |
| JP | 11-299477 | 11/1999 |
| JP | 2000-000468 A | 1/2000 |
| WO | 98/57152 | 9/1998 |

PARTICLE OR CELL ANALYZER AND METHOD

RELATED APPLICATIONS

This application is continuation of application Ser. No. 10/410,230 filed Apr. 8, 2003, which is a divisional application of application Ser. No. 09/844,080 filed Apr. 26, 2001, which claims priority to provisional application Ser. No. 60/230,380 filed Sep. 6, 2000.

BRIEF DESCRIPTION OF THE INVENTION

This invention relates generally to a particle or cell analyzer and method, and more particularly to a particle or cell analyzer and method in which the sample solution containing the particles or cells is drawn through a capillary for presentation to a shaped light beam.

BACKGROUND OF THE INVENTION

The detection and analysis of individual particles or cells is important in medical and biological research. It is particularly important to be able to measure characteristics of particles such as concentration, number, viability, identification and size. Individual particles or cells as herein defined include, for example, bacteria, viruses, DNA fragments, cells, molecules and constituents of whole blood.

Typically, such characteristics of particles are measured using flow cytometers. In flow cytometers, particles which are either intrinsically fluorescent or are labeled with a fluorescent marker or label, are hydrodynamically focused within a sheath fluid and caused to flow past a beam of radiant energy which excites the particles or labels to cause generation of fluorescent light. One or more photodetectors detect the fluorescent light emitted by the particles or labels at selected wavelengths as they flow through the light beam, and generates output signals representative of the particles. In most cytometers, a photodetector is also used to measure forward scatter of the light to generate signals indicative of the presence and size of all of the particles.

U.S. Pat. No. 5,547,849 describes a scanning imaging cytometer wherein an unprocessed biological fluid sample is reacted with a fluorescently labeled binding agent. The reacted sample undergoes minimal processing before it is enclosed in a capillary tube of predetermined size. The capillary tube with the enclosed sample is optically scanned and the fluorescent excitation is recorded from a plurality of columnar regions along the capillary tube. Each columnar region is generally defined by the spot size of the excitation beam and the depth dimension of the capillary tube. A spacial filter of sufficient pinhole diameter is selected to allow simultaneous volumetric detection of all fluorescent targets in each columnar region. The cellular components or particles are identified as is their concentration.

OBJECTS AND SUMMARY OF THE INVENTION

It is an object of the present invention to provide a particle analyzer and method having high particle selectivity.

It is another object of the present invention to provide a compact, high-sensitivity particle analyzer.

It is still another object of the present invention to provide a portable particle analyzer and method for use in immunology, microbiology, cell biology, hematology and cell analysis.

It is a further object of the present invention to provide a simple-to-use, less expensive, particle analyzing apparatus for counting particles in small volumes of sample fluids and determining their characteristics.

It is still another object of the present invention to provide a particle analyzer and method for analyzing low volumes of low-density sample fluids.

The foregoing and other objects of the invention are achieved by a particle analyzing apparatus which analyzes particles in a sample fluid flowing through a capillary tube which has a suspended sampling end for insertion into a sample fluid, and a pump coupled to the other end for drawing the sample fluid and particles through the capillary. An illumination source is provided for projecting a beam of light through a predetermined volume of the capillary to impinge upon the particles that flow through that volume. At least one detector is disposed to receive fluorescent light emitted by excited fluorescing particles and provide an output pulse for each fluorescing particle, and another detector senses the passage of all particles which flow through the volume and provides an output signal, whereby the output signals from the detectors can be used to characterize the particles.

A method of analyzing samples containing particles, which includes drawing the sample through a capillary volume where the particles are illuminated by a light source, and scattered light and fluorescent light from labeled particles excited by the light source is detected to provide output signals which are processed to provide an analysis of the sample.

BRIEF DESCRIPTION OF THE DRAWINGS

The foregoing and other objects of the invention will be more clearly understood from the following detailed description when read in conjunction with the accompanying drawings in which.

DESCRIPTION OF PREFERRED EMBODIMENT(S)

Figure 1:
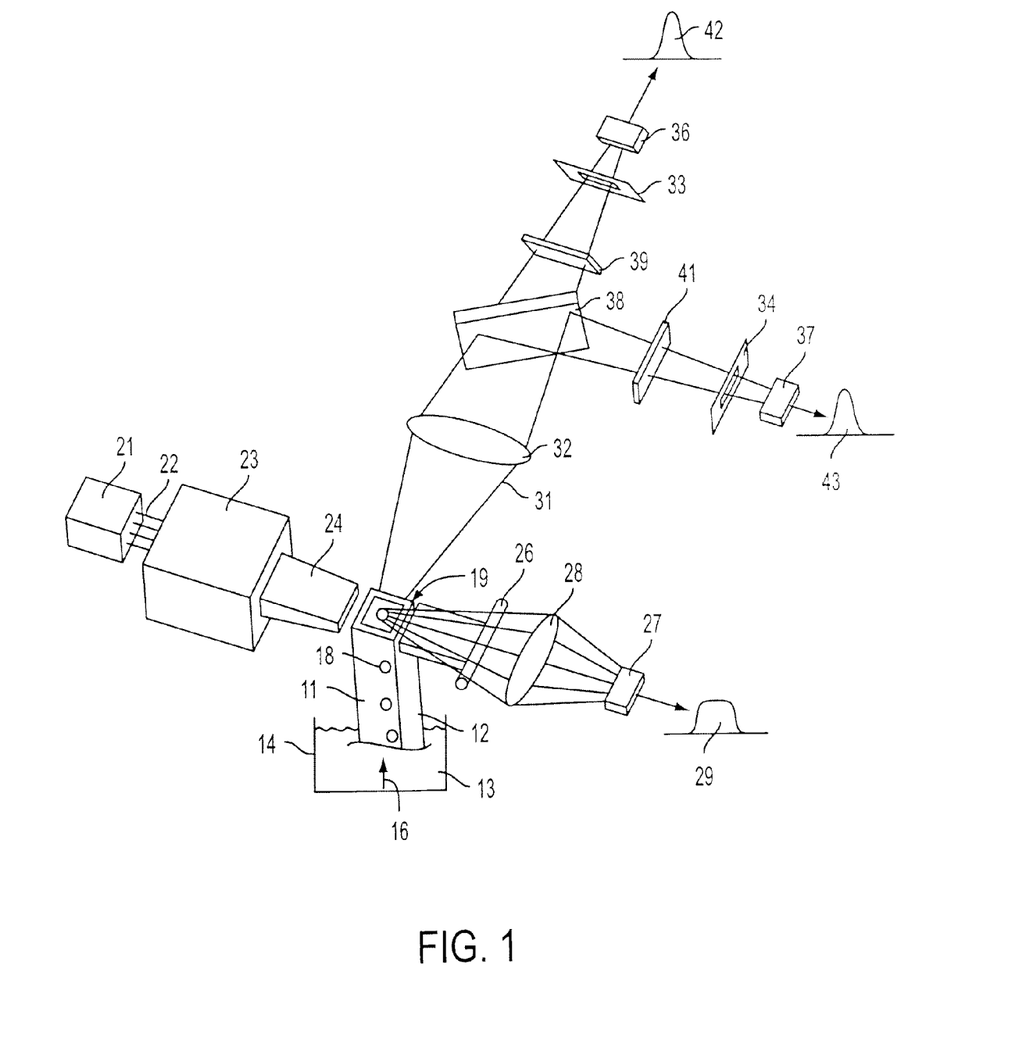
FIG. 1 schematically shows a particle analyzer in accordance with the present invention.
Figure 15:
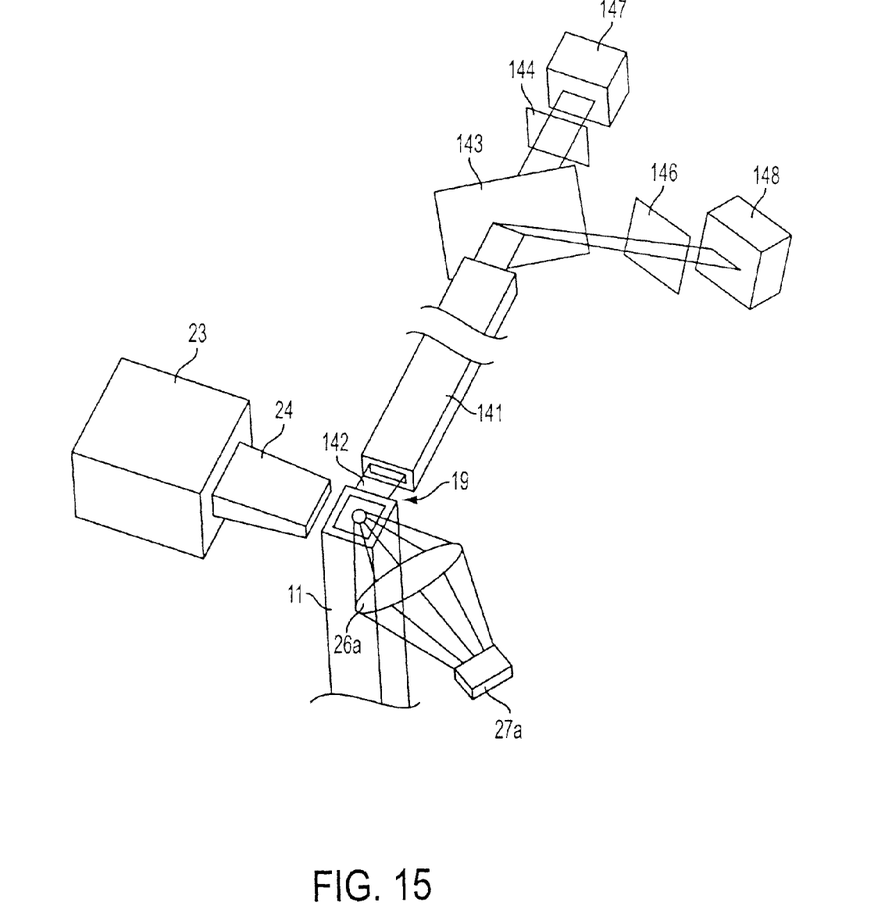
FIG. 15 shows a particle analyzer in accordance with another embodiment of the invention.

Referring to FIG. 1, there is schematically illustrated a particle analyzer in accordance with one embodiment of the present invention. As used herein, "particles" means particles or cells, for example, bacteria, viruses, DNA fragments, blood cells, molecules and constituents of whole blood. A capillary tube 11 has a suspended end 12 adapted to be immersed into a sample solution 13 retained in a cuvet or vial 14. It will be apparent that, although a square capillary is illustrated, the capillary may be cylindrical or of other shape, such as a microchannel. Sample fluid is drawn into the end of the capillary as shown by the arrow 16. As will be presently described, the fluid or liquid sample is drawn through the capillary by a calibrated pump connected to the other end of the capillary. The size or bore of the capillary tube 11 is selected such that the particles 18 are singulated as they pass a viewing or analyzing volume 19. A light source, preferably a laser, 21 emits light 22 of selected wavelength. The light is received by an optical focusing system 23 which focuses said light and forms and directs a beam 24 to the capillary where it passes through the analyzing volume 19. The optical focusing system is configured to form a flat, thin rectangular beam which impinges on the capillary tube 11. The thickness of the flat beam and the walls of the capillary define the analyzing volume. In order to count all particles which traverse the detection volume, that is particles which are tagged to fluoresce and untagged particles, scattered light is detected. In one embodiment, a beam blocker 26 is positioned to intercept the beam after it passes through the capillary tube 11. Light scattered by a particle that flows through the beam is directed onto a detector 27 by lens 28. The detector provides an output signal such as the one illustrated by the peak 29, when a particle passes through the beam and scatters the light. The size of the peak is dependent upon the size of the particle, and the occurrence of the peak indicates that a particle in the volume 19 (fluorescent or non-fluorescent) has traversed the thin beam of light. Another approach is to employ an off-axis detector, such as illustrated in FIG. 15, to measure the scattered light. In such event, a beam blocker is not required. There is also described below an impedance method of detecting particles.

Figure 2:
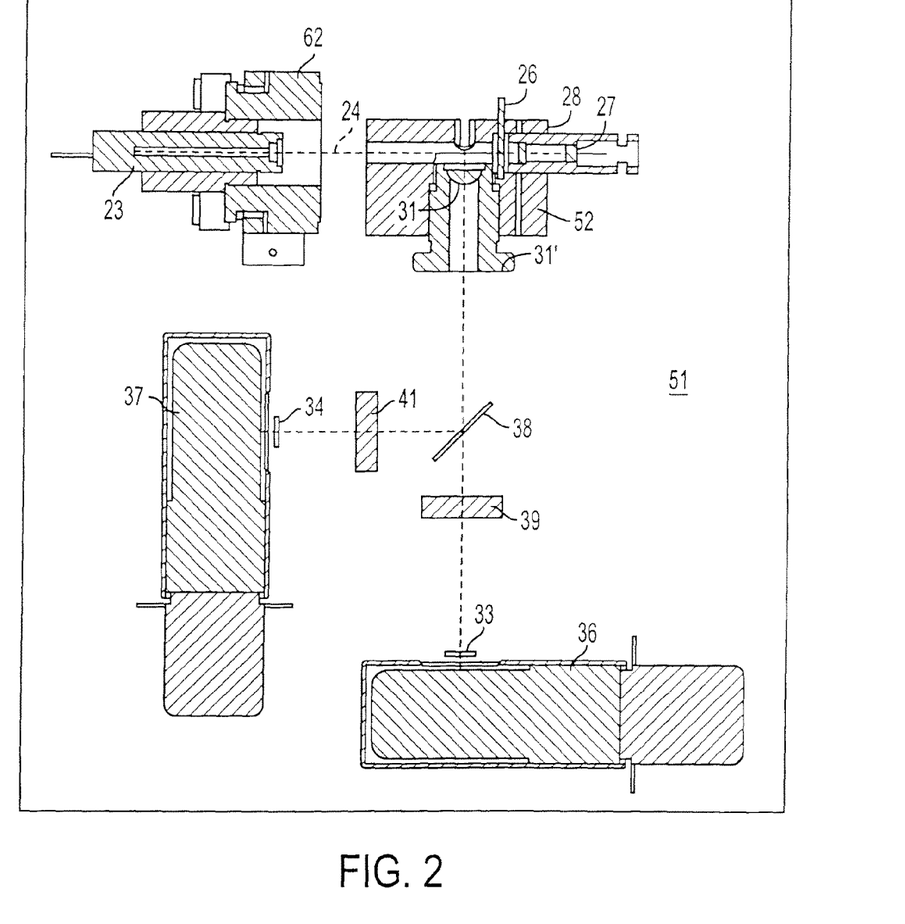
FIG. 2 is a top plan view showing the optical components shown in FIG. 1 mounted on a support shelf.
Figure 3:
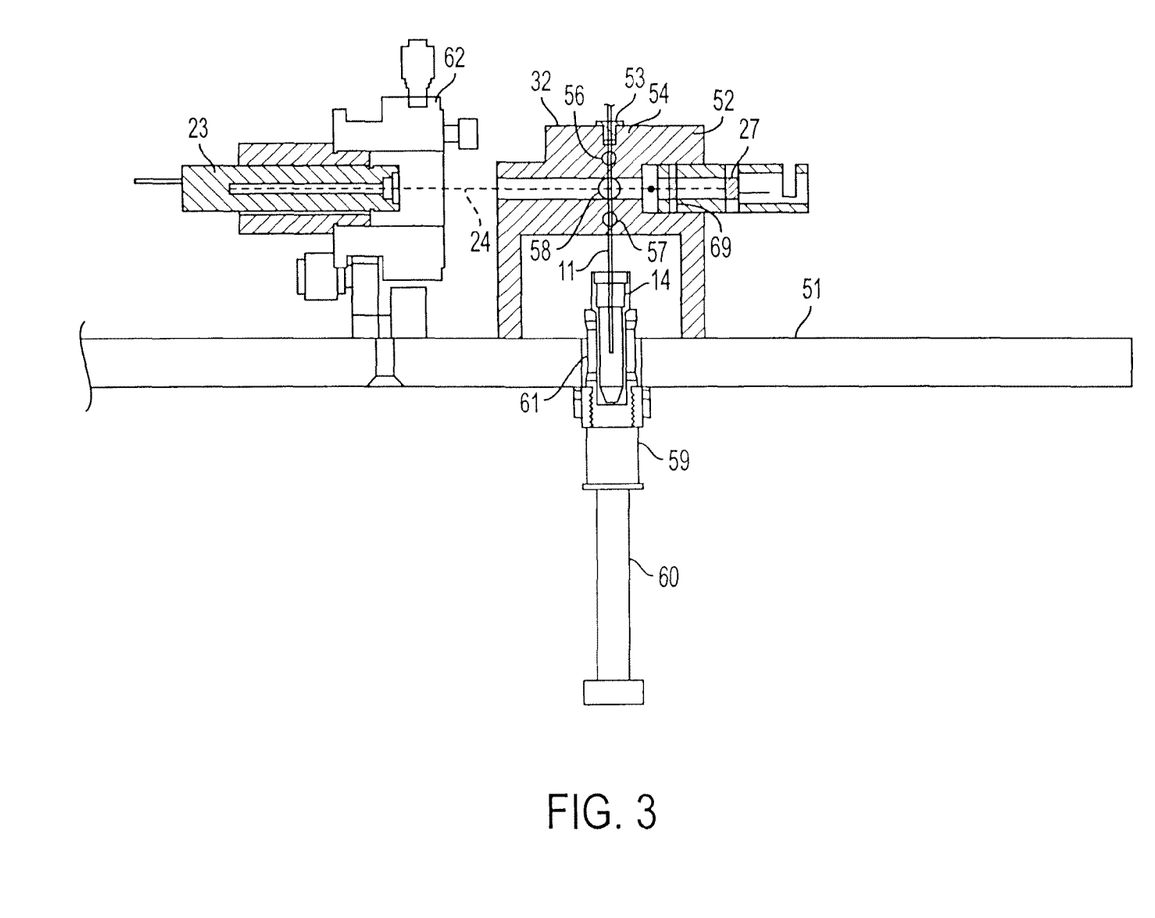
FIG. 3 is a front elevational view partly in section of FIG. 2.

If the particles are intrinsically fluorescent, or if the particles have been tagged with a fluorescent dye, they will emit light 31 at a characteristic wavelength as they pass through the volume defined by thin beam of light 24 which excites fluorescence. The fluorescent light is detected at an angle with respect to the beam axis so that no direct beam light is detected. In the embodiment of FIGS. 1-3, a collector lens 32 receives the fluorescent light from the particles and focuses it at detectors 36 and 37. We have found that initially we included slits 33 or 34 oriented in the direction of the thin beam to block any stray light. However, we have found that if the beam is properly focused into a thin flat beam, stray light is not a problem. This greatly simplifies assembly of the analyzer, since there is no need to carefully align the slits. The light impinges onto a dichroic beam splitter 38 which passes light of selected wavelengths through filter 39 to detector 36, and deflects light of other selected wavelengths through filter 41 to photodetector 37. For example, the dichroic beam splitter reflects light having wavelengths less than 620 nm, and transmits light having a greater wavelength. The filters 39 and 41 are selected to pass the wavelengths corresponding to the fluorescence wavelength expected from the fluorescing particles. In one example, the filters 39 and 41 were selected to pass light at 580 nm and 675 nm, respectively. This permitted identification and counting of particles which had been tagged with fluorescent material which emits at these wavelengths in response to the optical beam. The outputs of the photodetectors are pulses such as those schematically illustrated at 42 and 43, FIG. 1.

FIGS. 2 and 3 show the components of a particle analyzer in accordance with the above-described embodiment mounted on a support plate 51. The support plate 51 carries an optical block 52 adapted to receive and support the suspended capillary tube 11. Capillary tube 11 includes a hub 53, FIGS. 3 and 6, which is received in a well 54 to retain and position the capillary in the optical block. The capillary 11 is positioned in the optical block 52 by threading it through a narrow slot (not shown) and held in position by nylon-tipped set screws inserted in threaded holes 56 and 57. As it is inserted through the block, the capillary tube can be viewed through the viewing port 58. The end of the capillary tube is suspended and extends downwardly for insertion into a vial or cuvet 14 which contains the sample fluid or specimen. It is apparent that the capillary can be positioned and suspended by other supporting arrangements.

In one embodiment, a rotatable vial support member having two arms 59 is rotatably and slidably received by a guide post 60 secured to the base. A vial holder 61 is disposed at the end of each arm. In operation, the support is moved downwardly along the post 60, rotated to bring a vial under the capillary, and moved upwardly whereby the end of the capillary is immersed in the sample fluid. As the sample is being analyzed, another vial with another sample can be placed in the other holder whereby it can be brought into cooperative relationship with the capillary tip as soon as the analysis of the prior sample has been completed.

Figure 4:
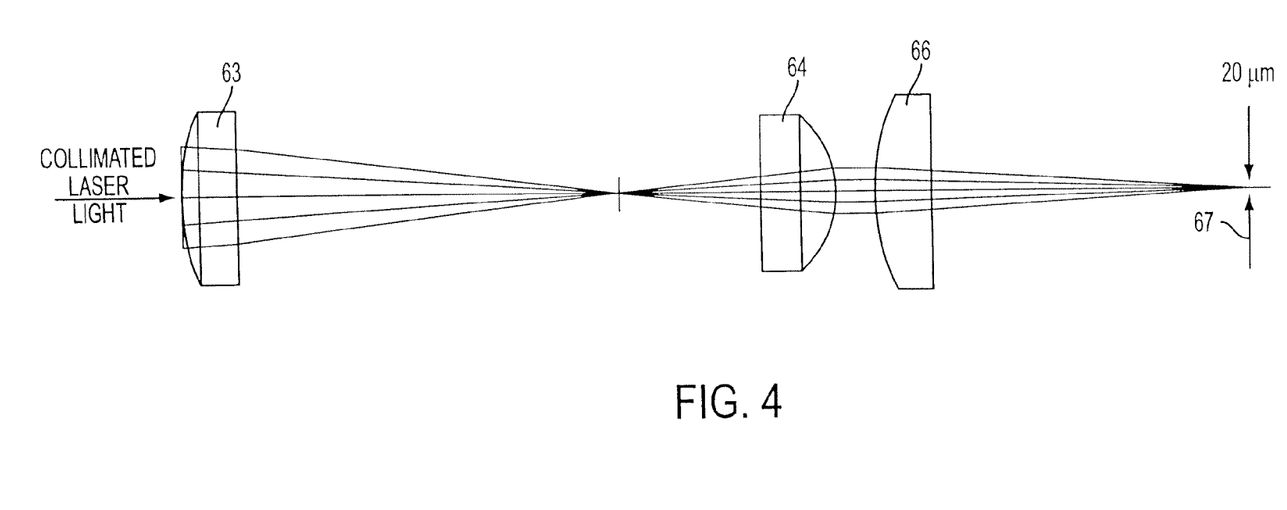
FIG. 4 is a side elevational view of the beam-forming optical system.
Figure 5:
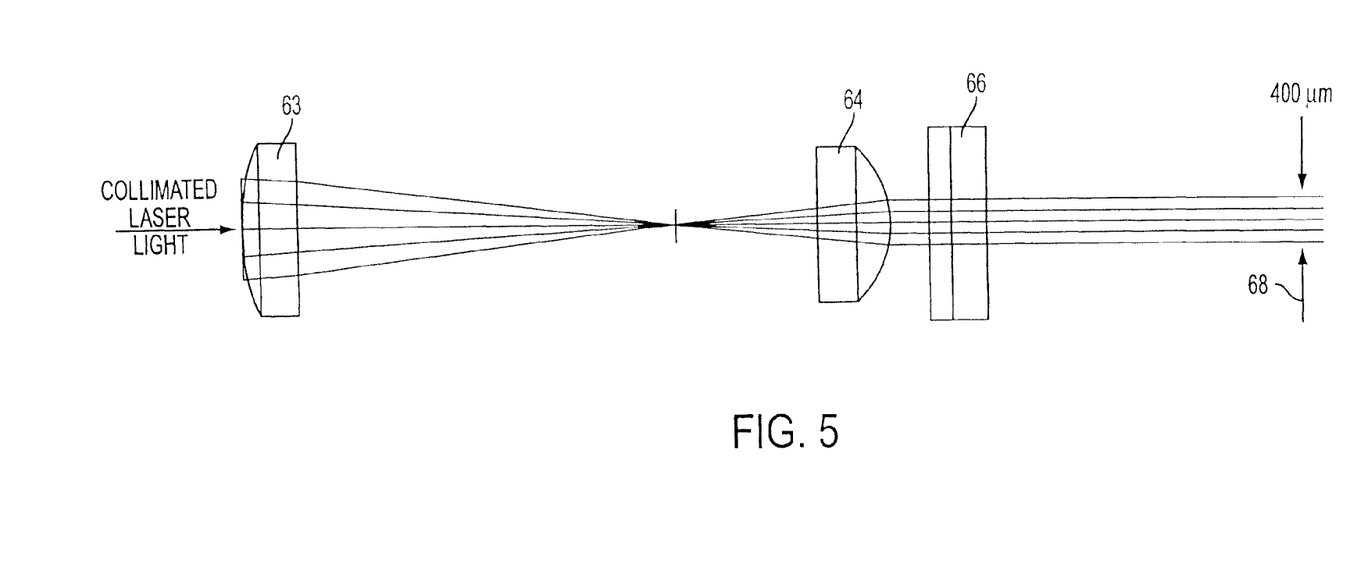
FIG. 5 is a top plan view of the beam-forming optical system of FIG. 4.

The housing 23 for the laser and optical focusing system which forms the beam 24 is carried on mounting block 62. The optical system is shown in FIGS. 4 and 5. It receives collimated light 22 from the laser 21, and generates the light beam 24, which impinges upon the capillary tube 11. The optical system may include, for example, a first plano-convex lens 63, a second plano-convex lens 64 and a cylindrical lens 66. The action of the lens assembly is to form a sheet-like thin rectangular beam which in one example was 20 µm in thickness along the longitudinal direction of the capillary, and 400 µm broad in the perpendicular direction, whereby a rectangular volume of sample was illuminated. The arrows 67 and 68, FIGS. 4 and 5, show the thin and broad configuration of the beam, respectively.

The photodetector 27 is mounted on the block 52 and supported axially with respect to the axis of the beam 24. The beam blocker bar 26 is mounted in the block 52 and intercepts and blocks out the direct beam after it passes through the capillary 11. The scattered light which passes around beam-blocking bar 26 is focused onto the detector 27 by a lens 28. Thus, the scattered light will provide an output signal for any tagged or untagged particle flowing past the observation volume 19, thus providing a total particle count. The output of the detector is then representative of the passage of a particle or cluster of particles and the size of the particle or cluster of particles. As will be explained below, this, taken together with the fluorescent signal, enables analysis of the sample. If the detector 27 is located off-axis, it will only receive scattered light and there is no need for a beam-blocking bar. Furthermore, this would be less sensitive to stray light in the forward direction which carries broadband laser noise which can mask out low level particle signals.

As described above, light emitted by fluorescence from intrinsically fluorescent particles, or particles which have been tagged with a fluorescent dye or material, is detected at an angle with respect to the beam axis. Referring to FIG. 2, the condenser lens 31 is carried by the block 52. The lens 31 receives the fluorescent light and focuses it at the detectors 36 and 37, which may be photomultipliers, charge-coupled diodes (CCDs), or other photodetectors. More particularly, the fluorescent light from the lens 31 impinges upon a dichroic beam splitter 38 which splits the beam into two wavelengths, one which passes through the beam splitter and one which is deflected by the dichroic beam splitter 38. Filters 39 and 41 filter the transmitted and reflected light to pass only light at the wavelength of the fluorescence of the particles to reject light at other wavelengths. If slits 33 and 34 are present, they reject any stray light from regions outside of the volume 19 defined by the thin rectangular beam 24. However, as discussed above, slits may not be required because the effect of stray light is minimized. The photo-multipliers or other photodetectors each provide an output signal representing the intensity of light at the filtered wavelength. As described above, the dichroic beam splitter reflects light having wavelengths less than 620 nm, and transmits light having greater wavelengths. The filter 39 passes light at 580 nm, while the filter 41 passes light at 675 nm. This permits analysis of particles which have been tagged with fluorescent substances which emit light at 580 nm and 675 nm to be individually counted. The output of the photo-multipliers are pulses 42 and 43, one for each particle emitting light at the particular wavelength, such as those schematically illustrated in FIG. 1. It is apparent that the wavelengths selected for the filters depends upon the fluorescent wavelength of the marker or label affixed to the particles.

In order to identify and count the particles in the fluid in a volumetric manner, the volume of fluid must be correlated with the number of particles detected in a given volume. In the present invention, the fluid sample is drawn through the capillary tube at a constant rate by an electrically operated calibrated pump or syringe 71, FIG. 6. The pump may be any other type of pump which can draw known volume samples through the capillary. The pump is connected to the capillary tube by a conduit or tube 72. This permits changing capillaries 11 to substitute a clean capillary or a capillary having a different diameter which may be needed for various types and sizes of particles or cells. As illustrated, the pump comprises a syringe pump in which sample fluid is drawn into the capillary by moving the plunger 73. The pump 71 is also connected to a waste or drain conduit 74 which includes a valve 76. When the valve is closed, the pump draws sample from the vial or cuvet through the capillary tube 11 past the detection volume 19. After an analysis has been completed, the valve 76 is opened, whereby reversal of direction of the plunger 73 causes fluid to flow through conduit 74 into the waste container 77. In accordance with a feature of the present invention, the diameter of the waste tube 74 is selected to be many times, 10 or more than that of the capillary, whereby substantially all of the fluid from the syringe is discharged into the waste. For example, if there is a factor of ten ratio in diameter, only 1/10,000 of the fluid will travel back through the capillary, a negligible amount.

Figure 6:
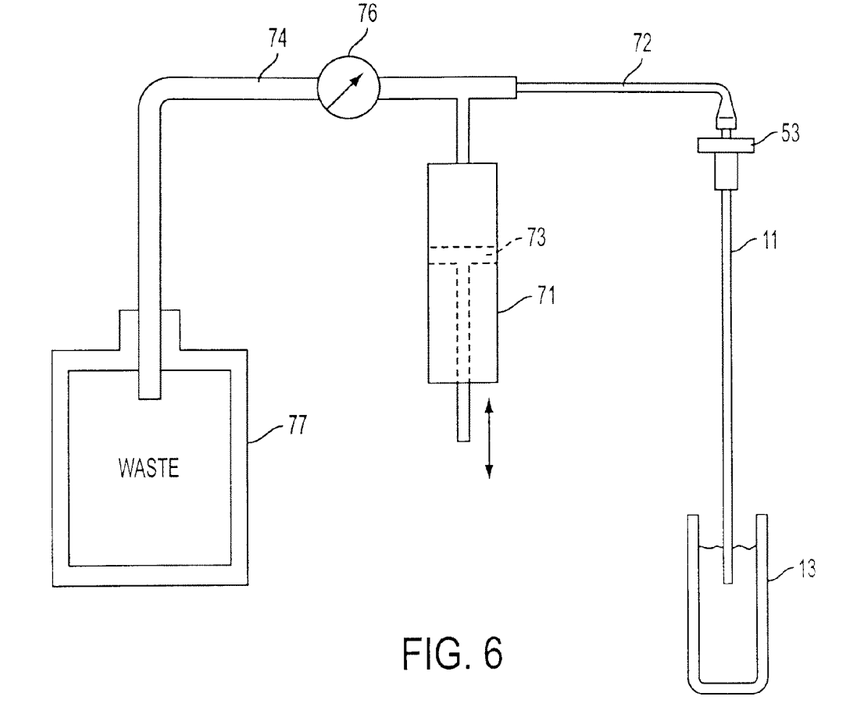
FIG. 6 shows the sample fluid flow and pumping system.

The pump is designed such that a predetermined movement of the plunger 73 will draw a known volume of sample through the capillary tube. The pump can be calibrated for each capillary by drawing a fluid into the pump by moving the plunger a known distance and then discharging the fluid and measuring the volume of the discharged fluid. Thereafter, for a given movement of the plunger, the volume of sample which flows through the analyzing volume is known. The volume can either be determined by measuring the movement of the plunger or measuring the time the plunger is moved if it is calibrated as a function of time. Although a syringe pump is described, other types of pumps which can draw known volumes of fluid through the capillary can be used.

Figure 7:
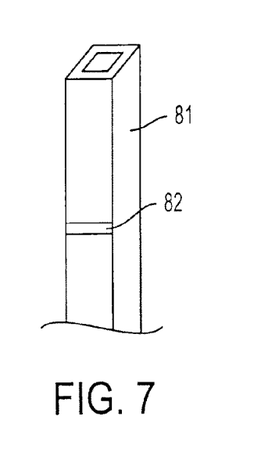
FIG. 7 is a perspective view of a portion of a capillary used in connection with one embodiment of the present invention.
Figure 8:
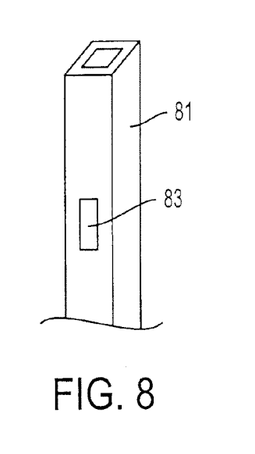
FIG. 8 is a perspective view of a portion of a capillary tube used in connection with another embodiment of the present invention.

Preferably, the capillary tubes are of rectangular configuration. FIGS. 7 and 8 show a capillary tube that includes an opaque coating 81 which is removed over an area 82, FIG. 7, or 83, FIG. 8. In the embodiment of FIG. 7, the beam projects through the window 82 which has a rectangular configuration to accept of the beam 24. In FIG. 8, the slit masks the walls of the capillary tube and prevents diffraction of light by the walls. A combination of the two masks would confine the detected light to that emitted by a particle traveling through the capillary to block out any stray light.

Figure 9:
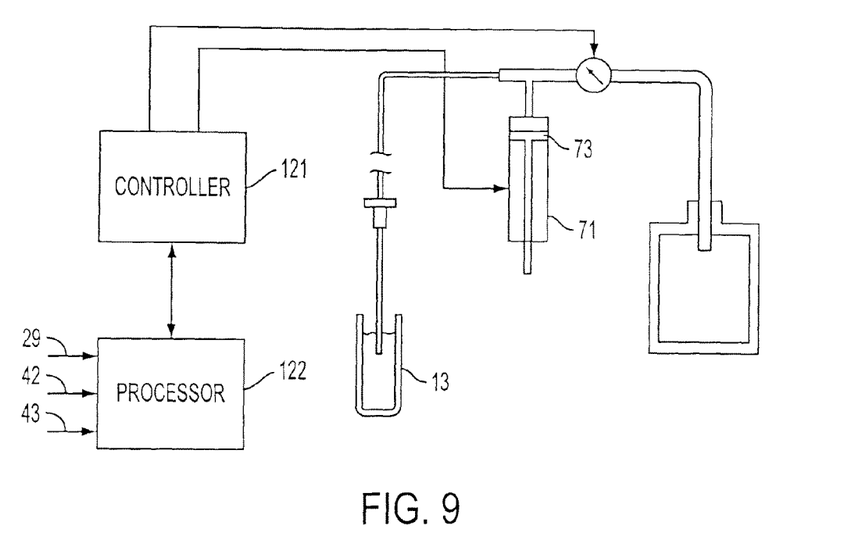
FIG. 9 schematically shows a control and data acquisition system associated with the particle analyzer.
Figure 10:
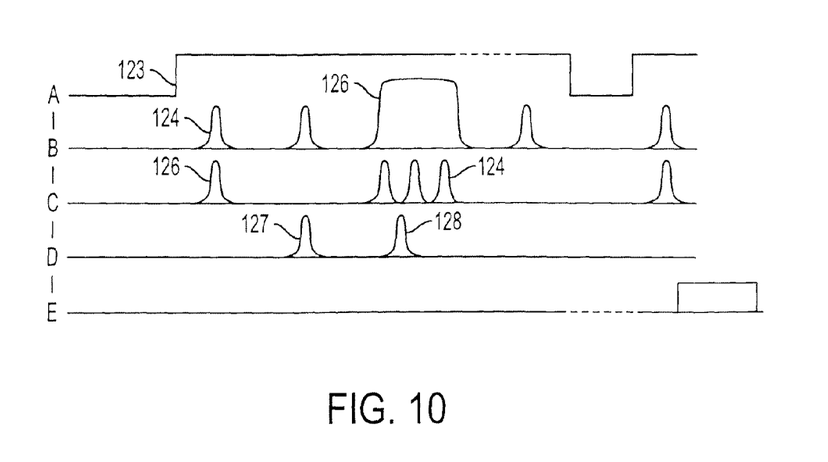
FIG. 10 is a timing and data acquisition diagram illustrating operation of the particle analyzer.

An example of the operation of the apparatus to analyze a sample containing particles which do not fluoresce, and particles which intrinsically fluoresce or are marked or tagged to fluoresce, at two different wavelengths, for example 580 nm and 675 nm, is now provided with reference to FIGS. 9 and 10.

With the syringe pump plunger 73 extended to empty the pump, the sample vial containing the particles is positioned to immerse the end of the capillary 11 in the sample. The sample is then drawn through the capillary by applying a control signal from the controller 121 to start the pump 71. The controller receives the command from processor 122. The pump 71 is driven at a constant rate whereby the volume of sample passing through the analyzing volume 19 can be measured by timing the counting period. After sample has been drawn from the vial for a predetermined time to assure that the new sample has reached the volume 19, the processor begins to process the output 29 from the scatter photodetector and the outputs 42 and 43 from the photodetectors and does so for a predetermined time which will represent a known volume of sample passing through the analyzing volume. The processing time is schematically illustrated in FIG. 10A by the curve 123. FIG. 10B illustrates the output pulses 28 from the scatter detector. It is seen that there are individual particles which provide a trace 124 and a cluster of particles which provides a trace 126. FIG. 10C shows traces 126 for particles which fluoresce at a first wavelength, for example 675 nm. Of note is the fact that the cluster 126 includes three such particles. FIG. 10D shows traces 127 for particles which fluoresce at another wavelength, for example 750 nm. Of note is the fact that there is also one such particle 128 in the cluster 126. The processor can call for a number of analyzing cycles. Finally, when an analysis is completed, the processor instructs the controller to open the valve 76 and reverse the pump to discharge the analyzed sample into the waste 77. A new sample cuvet can then be installed and a new sample analyzed. The processor can be configured to average the counts over a number of cycles and to process the counts to provide outputs representing the concentration of the various particles, the number of particles, etc. Using suitable labels or markers one can conduct viability assays and antibody screening assays or monitor apoptosis.

Figure 11:
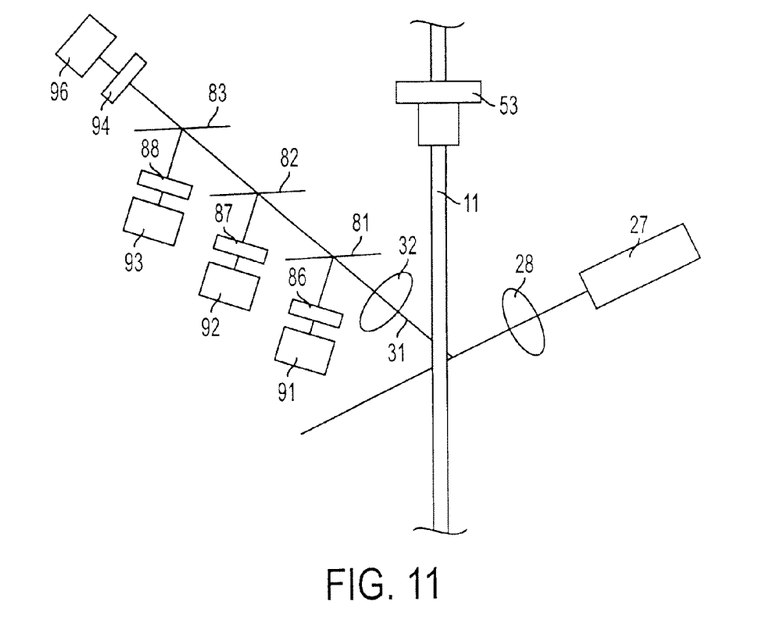
FIG. 11 is a schematic view of a four-color particle analyzer.

Although the apparatus has been described for a two-color analysis it can easily be modified for four-color analysis. This is schematically shown in FIG. 11. The input light beam 24 impinges upon the analyzing volume 19. The photodetector 27 and associated lens 28 provide the scatter signal. The fluorescent light 31 is focused by lens 32 to pass through three dichroic beam splitters 81, 82 and 83 which reflect light at three different wavelengths through filters 86, 87 and 88 onto photodetectors 91, 92 and 93. The light at the fourth wavelength, passed by the three dichroic beam splitters 81, 82 and 83 passes through filter 94 onto photodetector 96. Thus, up to four different particles which intrinsically fluoresce or are labeled to fluoresce at four different wavelengths can be analyzed by choosing the proper reflecting wavelengths for the dichroic beam splitter and the filters.

Figure 12:
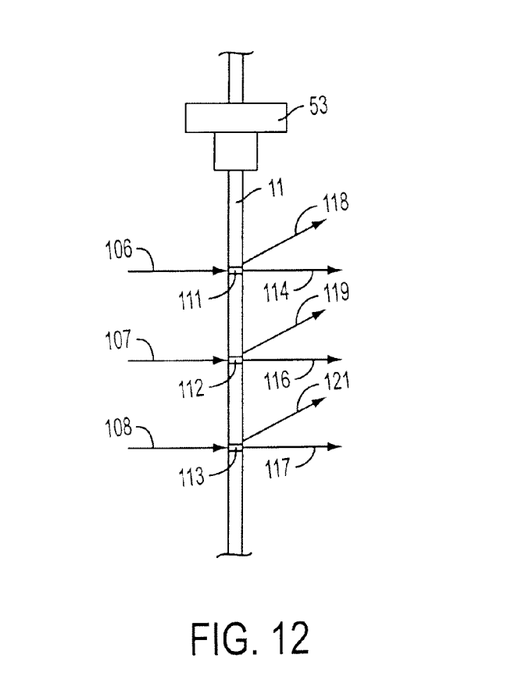
FIG. 12 schematically illustrates an analyzer having multiple analyzing stations along the capillary tube.

FIG. 12 schematically shows a system using a plurality of light sources (not shown) projecting light beams 106, 107 and 108 to analyzing volumes 111, 112 and 113, which are at a predetermined distance apart. The scattered light indicated by arrows 114, 116, 117 is detected by individual detecting systems of the type described. The fluorescent light represented by arrows 118, 119 and 121 is detected by individual analyzing systems of the type described above. This arrangement permits analyzing particles which have been tagged with different labels by selecting the wavelength of the light source to excite different fluorescent tags or markers. Alternatively, the plurality of light beams may project onto a single analyzing volume and the individual analyzing systems receive the different fluorescent wavelengths.

Figure 13:
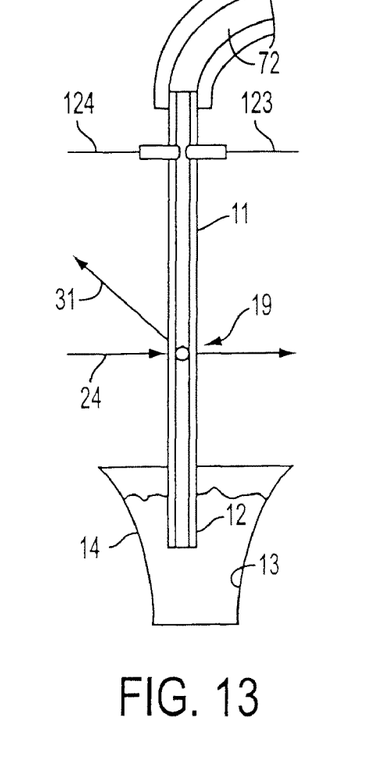
FIG. 13 shows an impedance detector for detecting particles as they flow past a detection region.
Figure 14:
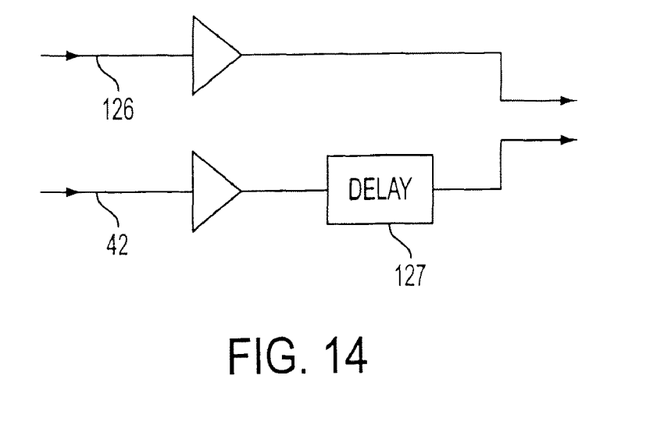
FIG. 14 schematically shows a circuit suitable for correlating signals from an impedance cell sensor with photomultiplier output signals

Rather than sensing particles by light scattered by the particles, a change in electrical current can detect the particles as they travel past spaced electrodes disposed on opposite sides of the flow path. Referring to FIG. 13, a capillary 11 is shown with spaced electrodes 123 and 124 which extend into the capillary 11. The electrodes are spaced along the capillary from the analyzing volume 19. As the cell or particle flows between the electrodes, the electrically conductive working fluid is displaced and the resulting change in current (impedance) can be detected. This method avoids any laser noise problem. It is usually most convenient mechanically to place the electrodes along the fluid flow path either before or after the point where the laser beam 24 impinges onto the capillary. This creates a timing problem in that the impedance detector will detect a cell at a different point in time than the fluorescence detector, and it is possible that a second cell near the first may create a signal in the fluorescence detector at the same time as the first cell creates a signal in the impedance channel. This necessitates the use of a delay element to shift one signal in time with respect to the other by an amount equal to the distance between the two detectors divided by the flow rate, so that the two signals from one cell become congruent. This delay element may be implemented in hardware with a delay line or circuit. FIG. 14 shows the output signal 126 from the impedance cell sensor and the fluorescent signal 42 or 43 (FIG. 1) with a delay 127 in the photomultiplier signal, whereby the signals are correlated. This can also be implemented in software by sampling the signal from each detector into its own data stream and then shifting one data stream with respect to the other. A further feature of this arrangement is that, if the physical distance between the two detectors is known, then the actual flow rate can be deduced by finding the delay that corresponds to the best correlation between the two channels; this might be helpful when trying to identify a clogged capillary.

As explained above, we have discovered that because the illumination traversing the capillary is in the form of a thin rectangular beam the detection volume is accurately defined by the thickness of the beam and the walls of the capillary 11. With this in mind, we conducted experiments in which the slits 33 and 34 were eliminated. We found that the results obtained in tests of variously labeled particles were comparable to those obtained with slits. Referring to FIG. 15, an embodiment of the invention making use of this discovery is schematically illustrated. The particle detector includes a light source, for example a laser, whose output is optically focused by the optics 23 to form a thin, flat beam 24 as described above. The beam traverses the capillary 11 to define the detection volume 19. The scatter detector includes an off-axis detector assembly including a collection lens 26a and a detector 27a. As much as possible of the emitted fluorescent light from the tagged cells or particles is gathered or intercepted by an off-axis detector assembly. It can be gathered by a condenser lens as illustrated in FIG. 1. However, in the present embodiment, it is collected by a light guide 141 which receives the light 142 and conveys it to the beam splitter 143. The light beam is directed to optical filters 144 and 146 and directly to detectors 147 and 148. The output signals from the detectors and the scatter signals are processed to provide particle counts, cell viability, antibody screening, etc.

There has been provided a simple-to-use particle analyzing apparatus for characterizing particles such as determining their count, viability, concentration and identification. The analyzing apparatus detects particles in a sample fluid flowing through a capillary tube which has a sampling end for insertion into a sample fluid, and a pump coupled to the other end for drawing sample through the capillary. A light source is provided for projecting a beam of light through a predetermined analyzing volume of the capillary tube to excite fluorescence in particles that flow through the volume. At least one detector is disposed to receive the fluorescent light from excited particles and another detector is disposed to provide a signal representing all particles which flow through the analyzing volume. The output of said detectors provides signals which can be processed to provide the characteristics of the particles.

The foregoing descriptions of specific embodiments of the present invention have been presented for purposes of illustration and description. They are not intended to be exhaustive or to limit the invention to the precise forms disclosed, and obviously many modifications and variations are possible in light of the above teaching. The embodiments were chosen and described in order to best explain the principles of the invention and its practical application, to thereby enable others skilled in the art to best use the invention and various embodiments with various modifications as are suited to the particular use contemplated. It is intended that the scope of the invention be defined by the claims appended hereto and their equivalents.

What is claimed is:

1. A particle analyzing apparatus comprising:
 a capillary tube having a first end portion, a second opposite end portion, and a predetermined internal cross-sectional area, said first end portion being adapted to be suspended for immersion into a sample fluid containing particles to be analyzed;
 one or more holders for holding one or more sample fluids, said one or more holders being movable relative to the first end portion of the capillary tube;
 a source of light;
 an optical system configured to receive and focus the light from said source to form and direct a rectangular beam through the capillary tube to define an analyzing region in the capillary tube;
 a pump connected to the second end portion of the capillary tube, said pump being adapted to draw a volume of a sample fluid through the first end portion into the capillary tube and passing through said analyzing region;
 at least one first detector for detecting fluorescent light emitted by particles excited by said beam in said analyzing region;
 a valve coupled to the pump, the second end portion of the capillary tube and a waste dump, wherein when the valve is closed, the pump draws the sample fluid from the first end portion through said capillary tube, and when the valve is opened the pump discharges the fluid sample previously drawn through the capillary tube to the waste dump;

wherein the pump is coupled to the waste dump via a conduit which has a diameter substantially greater than a diameter of the capillary tube.

2. The particle analyzing apparatus of claim 1 wherein the diameter of the conduit is about 10 times or more than the diameter of the capillary tube.

3. A particle analyzing apparatus comprising:

a capillary tube having a first end portion, a second opposite end portion, and a predetermined internal cross-sectional area, said first end portion being adapted to be suspended for immersion into a sample fluid containing particles to be analyzed;

one or more holders for holding one or more sample fluids, said one or more holders being movable relative to the first end portion of the capillary tube;

a source of light;

an optical system configured to receive and focus the light from said source to form and direct a rectangular beam through the capillary tube to define an analyzing region in the capillary tube;

a pump connected to the second end portion of the capillary tube, said pump being adapted to draw a volume of a sample fluid through the first end portion into the capillary tube and passing through said analyzing region;

at least one first detector for detecting fluorescent light emitted by particles excited by said beam in said analyzing region;

wherein said capillary tube comprises a substantially straight section, said substantially straight section including the first end portion adapted to be suspended for immersion into a sample fluid, and the analyzing region is defined in the substantially straight section; and a block having a passageway adapted to receive at least a portion of the capillary tube, said block comprises means for positioning the capillary tube and allows the suspended first end portion to be immerged into a sample fluid held in one of the one or more holders.

4. The particle analyzing apparatus of claim 3 wherein said block is provided with an opening recess configured to receive a hub member, said hub member is configured to retain the capillary tube in the block.

5. A particle analyzing apparatus comprising:

a capillary tube having a first end portion, a second opposite end portion, and a predetermined internal cross-sectional area, said first end portion being adapted to be suspended for immersion into a sample fluid containing particles to be analyzed;

one or more holders for holding one or more sample fluids, said one or more holders being movable relative to the first end portion of the capillary tube;

a source of light;

an optical system configured to receive and focus the light from said source to form and direct a rectangular beam through the capillary tube to define an analyzing region in the capillary tube;

a pump connected to the second end portion of the capillary tube, said pump being adapted to draw a volume of a sample fluid through the first end portion into the capillary tube and passing through said analyzing region;

at least one first detector for detecting fluorescent light emitted by particles excited by said beam in said analyzing region;

wherein said capillary tube comprises a substantially straight section, said substantially straight section including the first end portion adapted to be suspended for immersion into a sample fluid, and the analyzing region is defined in the substantially straight section, wherein said substantially straight section of the capillary tube is disposed substantially vertical with respect to the ground;

wherein said one or more holders are vertically moveable.

6. The particle analyzing apparatus of claim 5 wherein said one or more holders are rotatable around the capillary tube.

7. A particle analyzing apparatus comprising:

a capillary tube having a first end portion, a second opposite end portion, and a predetermined internal cross-sectional area, said first end portion being adapted to be suspended for immersion into a sample fluid containing particles to be analyzed;

one or more holders for holding one or more sample fluids, said one or more holders being movable relative to the first end portion of the capillary tube;

a source of light;

an optical system configured to receive and focus the light from said source to form and direct a rectangular beam through the capillary tube to define an analyzing region in the capillary tube;

a pump connected to the second end portion of the capillary tube, said pump being adapted to draw a volume of a sample fluid through the first end portion into the capillary tube and passing through said analyzing region;

at least one first detector for detecting fluorescent light emitted by particles excited by said beam in said analyzing region; and wherein said optical system is configured to form and direct a sheet-like rectangular beam having a thickness of about 20 μm and a width of about 400 μm through the capillary tube.

* * * * *